United States Patent [19]
Stitzel et al.

[11] Patent Number: 5,625,194
[45] Date of Patent: Apr. 29, 1997

[54] CONTINUOUS CLEANING OF LAMP WELLS FOR ULTRAVIOLET (UV) LIGHT PRODUCING LAMPS

[75] Inventors: Robert K. Stitzel, Fritch; C. Stewart Denton, Borger, both of Tex.

[73] Assignee: Phillips Petroleum Company, Bartlesville, Okla.

[21] Appl. No.: 546,383

[22] Filed: Oct. 20, 1995

[51] Int. Cl.$^6$ ................................. G01N 21/00
[52] U.S. Cl. ............................. 250/431; 250/436
[58] Field of Search ...................... 250/431, 436; 422/24

[56] References Cited

U.S. PATENT DOCUMENTS

| | | | |
|---|---|---|---|
| 3,456,107 | 7/1969 | Robertson | 250/431 |
| 3,462,597 | 8/1969 | Young | 250/43 |
| 3,519,817 | 7/1970 | Brunner | 250/436 |
| 3,562,520 | 2/1971 | Hippen | 250/43 |
| 3,775,041 | 11/1973 | Buttner | 432/27 |
| 3,869,525 | 3/1975 | Miller | 260/873 |
| 3,904,363 | 9/1975 | Free | 250/431 |
| 4,034,219 | 7/1977 | Louden et al. | 250/301 |
| 4,291,550 | 9/1981 | Engdahl et al. | 62/544 |
| 4,554,965 | 11/1985 | Bochinski et al. | 165/95 |
| 4,728,368 | 3/1988 | Pedziwiatr | 134/1 |
| 4,899,056 | 2/1990 | Ellner | 250/431 |

*Primary Examiner*—Bruce C. Anderson
*Attorney, Agent, or Firm*—George E. Bogatie

[57] ABSTRACT

Tubular lamp wells used to protect ultraviolet light producing lamps mounted in a photochemical reactor are continuously cleaned, while a reaction is being carried out, by containing a large number of small, chemically inert plastic pellets in the reaction solution. The plastic pellets are dispersed in the reaction solution and maintained in turbulent motion by a stirrer in the reactor. In use, the pellets frequently impact the outer surface of the tubular wells with sufficient momentum to prevent deposits of material, which could discolor the surface, from adhering on the tubular wells.

20 Claims, 2 Drawing Sheets

CONTINUOUS CLEANING OF LAMP WELLS FOR ULTRAVIOLET (UV) LIGHT PRODUCING LAMPS

This invention relates to photochemical reactors, and more particularly to method and apparatus for cleaning of lamp wells in the reactor which surround ultraviolet light lamps used for promoting a chemical reaction.

BACKGROUND

Essentially all of the primary mercaptans are made commercially in the United States by the ultraviolet light promoted addition of $H_2S$ to 1-olefins. A typical batch reactor for a mercaptan includes a large vessel containing an appropriate number of long cylindrical mercury vapor lamps, each of which is surrounded by a tubular quartz well that is immersed in the reaction solution. The contents of the reactor are energetically stirred, and the reaction can be batch or continuously operated. Commercial operation of such reactors, however, results in a large amount of heat produced by the ultraviolet lamps, which is mostly removed by water flowing in a jacket surrounding the reactor.

In reactors of this kind the intensity of the ultraviolet light reaching the reaction mass is often reduced by discoloration of the quartz well due to soot buildup on its outer surface. Accordingly, the efficiency of the lamp is greatly diminished by prolonged use. After a relatively short period of time the reactor is no longer efficient for producing the desired product, and eventually the reaction rate retards to a point where the reactor must be shut down so that maintenance crews can enter the reactor and manually clean the lamp wells.

Attempts to keep the lamp wells clean by circulating cleaning solution in the reactor have met with little success. A large number of cleaning fluids have been suggested for circulating in the reactor to continuously clean the lamp wells. Trial solutions consisted of: hydrocarbons including: pentane, o-xylene, isooctane, and hydrofluoric heavy alkylate; ketones including: acetone, and methyl isobutyl ketone; other compounds including: methyl tertiary-butyl ether, t-butyl disulfide, 1,1,1-trichloroethane, n-methyl pyrrolidone, ethylene glycol and glycerin; aqueous solutions including: 5% NaOH, 5% $Na_2S_2O_3$, 5% $Na_2CO_3$, and 2% NaOH; mixtures including: toluene/sulfolane, 30% $H_2O_2$ and detergent, and $Na_2PO_4$ and detergent; other solutions including: Dextron II transmission fluid, and type F transmission fluid. It is further known that other types of cleaning systems for UV lamp wells, which are not thought to be useful in photochemical reactors, have been proposed. For example, automatically controlled scraping devices may be employed to scrape deposits off of the UV lamp wells employed in water purification systems.

Accordingly, a long felt need remains for an effective method for continuously cleaning of the UV lamp wells in the photochemical reactor using mercury vapor or other UV light producing lamps for promoting a chemical reaction.

It is an object of this invention to increase production from a photochemical reactor by sustaining the initial reaction rate for a longer period of time.

It is another object of this invention to decrease downtime maintenance required in operating a photochemical reactor.

It is a more specific object of this invention to provide a self cleaning system which continuously clean lamp wells while the reactor is operating so as to maintain a high efficiency for the photochemical reaction.

It is another object to provide a cleaning system for UV reactor lamp wells which is both durable and economical of construction.

Still another object is to allow the operator of the reactor to schedule downtime for maintenance without considering unpredictable fouling time of the ultraviolet lamp wells.

SUMMARY OF THE INVENTION

According to the present invention, the foregoing and other objects and advantages are attained by a method of continuously cleaning lamp wells in a photochemical reactor, where a large number of small solid bodies ranging in volume from about 0.001 cc to about 100 cc, hereinafter referred to as pellets, are introduced into the reactor for suspension in a reaction solution contained in the reactor. The pellets are maintained in continuous turbulent motion in the reaction solution so as to cause frequent impacts with the outer surface of the tubular lamp wells thus maintaining an abrasive action between the pellets and the surface of the protective lamp wells. In use, the impacts of the pellets against the protective tubular lamp well are effective for preventing deposits from adhering on the lamp wells, which deposits, if not removed or prevented, would discolor the surface and reduce the intensity of ultraviolet light reaching the reaction solution.

In accordance with another aspect of the invention, the apparatus comprises a photochemical reactor having an inner wall which defines a chamber, at least one ultraviolet lamp positioned for illumination of the chamber, and a large number of pellets for containment in the chamber. A protective tubular lamp well, which is maintained in a transparent condition by the method of this invention, surrounds the ultraviolet light. A stirrer, supported for rotation in the chamber, generates sufficient turbulence of the reaction solution to cause the pellets, which will be suspended in the solution, to frequently impact the outer surface of the tubular lamp well with sufficient momentum for preventing deposits of soot from forming on the surface of the lamp wells.

Still other objects and advantages of this invention will become readily apparent to those skilled in this art from the following detailed description, wherein there is disclosed only the preferred embodiment of the invention, simply by way of illustration for the best mode presently contemplated for carrying out the invention.

The method and apparatus of the invention, using the large number of pellets, thus maintains initial reaction rates for a longer period of time. The probability of shutting down the reactor due to soot buildup on the lamp wells for the UV light sources is relatively remote.

DETAILED DESCRIPTION OF THE PREFERRED EMBODIMENT

Figure 1:
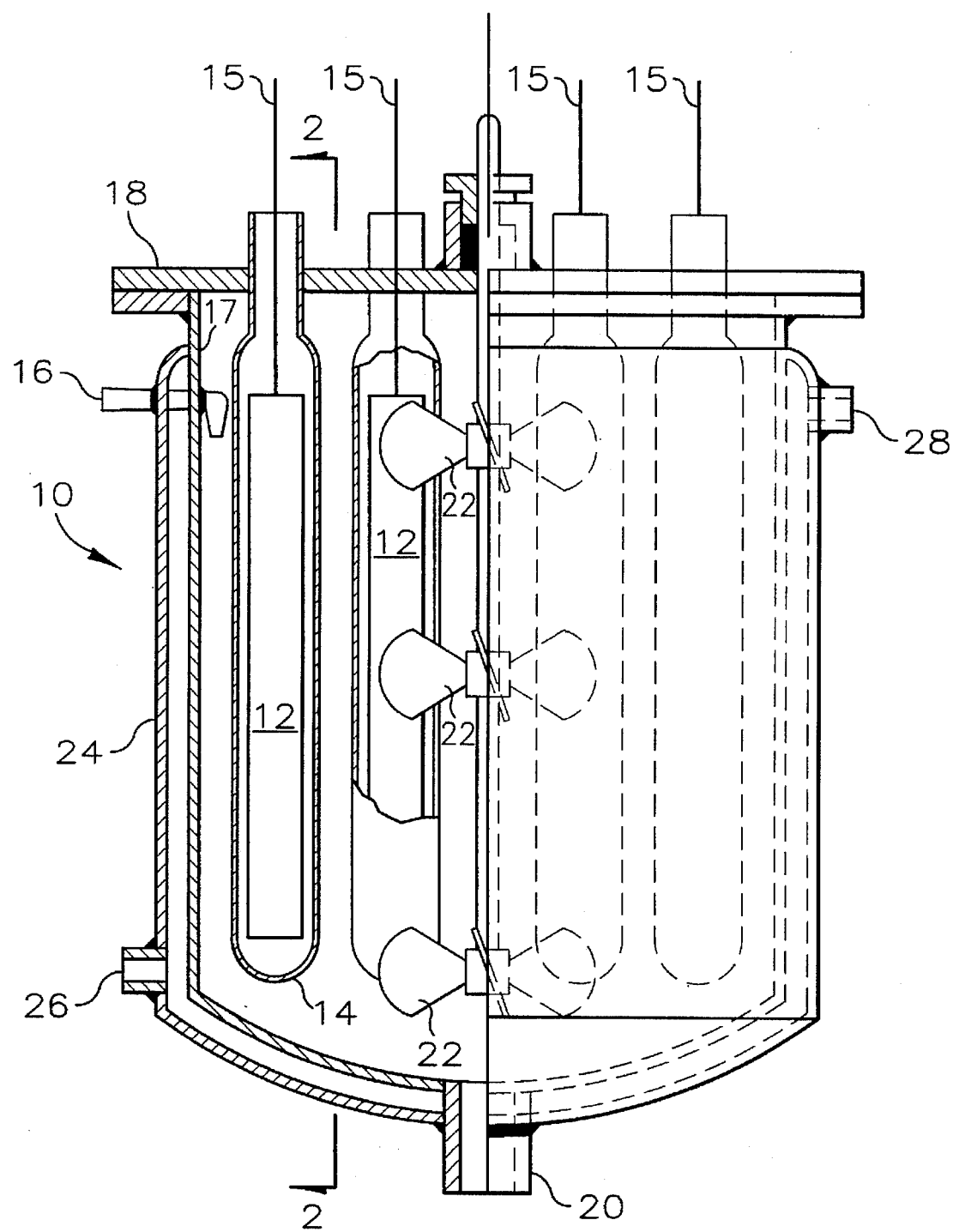
FIG. 1 is an elevation, partly in cross section, illustrating a batch photochemical reactor.

The present invention can be carried out in any photochemical reactor using an ultra-violet light source immersed in the reaction solution. The reaction system will be described with reference to a batch photochemical reactor as illustrated in FIG. 1. It is noted, however, that with little modification the invention is also applicable to continuously operated reactors.

Conventionally, a photochemical reaction can comprise the UV light promoted addition of $H_2S$ to 1-olefins, and in order for the photochemistry to be commercially useful, a photochemical lamp must have characteristics of high intensity in the desired spectral region, long life, stability of output, ease of operation and proper physical dimensions for the process under consideration. Of the various lamps commercially available, mercury arc lamps best meet all of these requirements.

Referring now to FIG. 1 in greater detail, the apparatus of the invention includes a reactor generally indicated at 10, having a container section 17 and a removable cover 18. The reactor is furnished with a plurality of elongated electric lamps 12 which are mounted in protective tubular quartz wells 14. The lamps 12 may be of a well-known type such as mercury vapor lamps for producing UV light, and the lamps having at their ends usual sockets or connectors members for wires 15 by which electric current is supplied to the lamps 12. The lamps 12 may be supported in the reactor by any suitable means, and usually extend through a removable cover 18 of the container 17. The arrangement of the lamps 12 is such that a reaction solution to be catalyzed is exposed to the UV light in the reactor. In batch reactors, measured quantities of reactants are charged usually in discrete quantities, and allowed to react for a given time under predetermined controlled conditions. One reactant can be added as it is consumed via inlet 16 if it differs in phase from the other materials. Reaction products exit the container 17 via outlet 20, while the pellets may be prevented from exiting the container 17 by any suitable means such as a screen (not illustrated) covering the outlet 20. Further the reactor is furnished with a plurality of stirrer elements 22 which are mounted in any suitable means for rotation in the container 17. The container 17 is surrounded by an external jacket 24 having a heat exchange input 26 and a heat exchange output 28 for removing the large amount of heat by circulating a cooling fluid such as water to remove the excess heat which may be produced in the container 17.

Figure 2:
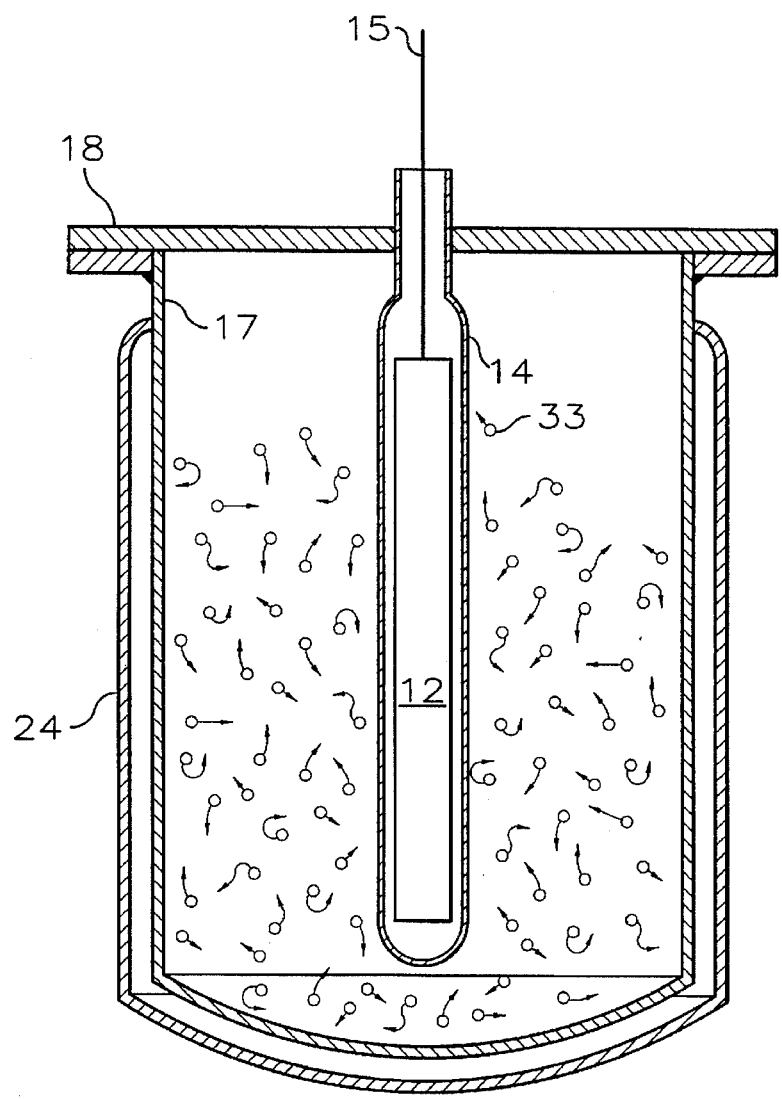
FIG. 2 is a cross sectional view taken along lines 2—2 of FIG. 1 illustrating turbulent motion of the pellets according to this invention.
Figure 3:
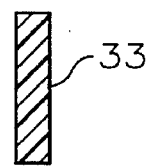
FIG. 3 is an elevation of one of the particles illustrated in FIG. 2.

In order to maintain the outer surface of the protective tubular quartz well 14 in a clean condition, thus preventing reduction of the intensity of the UV light reaching the reaction solution, a large number of pellets is introduced into the container 17. Referring now to FIG. 2, where like reference numerals indicate the same element shown in FIG. 1, there is illustrated the turbulent motion of the pellets 33 inside the container 17, where the turbulent motion causes frequent impacts between the pellets 33 and the protective tubular cylinders 14. The motion of the pellets 33 is maintained by rotation of the multiple stirrer elements 22 which are rotated by conventional means, not illustrated, at a rate sufficient to cause impacts of the pellets with the protective tubular cylinder 14 with a momentum which is effective for preventing soot from depositing on the outer surface of the protective cylinders 14.

The pellets may be of any desired shape such as spherical, cylindrical, conical, elliptical, rectangular and disc shape, and must be of sufficient hardness and durability in the reaction solution so that they may be reused a number of times while essentially retaining their original dimensions and hardness. The pellets can be prepared by any suitable technique, such as extrusion, pelletizing, molding, injection molding, and the like. The size and specific gravity of each pellet 33 can vary over a wide range, however, these parameters must be such that the pellets can be suspended and easily circulated in the reaction solution. The present invention contemplates cylindrically shaped plastic pellets made of highly abrasion resistant plastics such as polyethylene, polymethylpentene (PMP), and mixtures thereof which may be modified to contain a minor portion such as about 1 or 2 weight percent carbon black to improve UV stability. These plastics are preferred because their density is close to many products formed in UV reactors thus insuring good dispersion in the reaction solution.

The presently preferred size of the cylindrically shaped plastic pellets can range from about 0.00019 cubic inches (0.003 cc) to about 6.28 cubic inches (103 cc), more preferable, however, is a range from about 0.006 cubic inches (0.01 cc) to about 0.003 cubic inches (0.05 cc). The specific gravity of the pellets can also vary over a wide range depending, e.g., on the particular product of the reactor. A range such as from about 0.6 to about 1.4 is contemplated. Preferably, however, the specific gravity will range from about 0.7 to about 1.3, and most preferably from about 0.80 to about 1.0.

The number of pellets 33 charged to the container 17 is preferably chosen as the minimum number that effectively maintains cleanliness of the exterior surface of tubular lamp wells 14 during a reaction. Accordingly this number can vary over a wide range, such as from about $\frac{1}{1500}$ of the volume of the container 17 to about $\frac{1}{4}$ of the volume.

EXAMPLE I

The following example is provided to illustrate the use of small cylindrically shaped pieces of polymethylpentene (PMP) to remove soot deposited on the outside surface of a quartz lamp well during operation of a commercial size reactor. A soot covered lamp well was removed from service in a commercial size reactor and stored in atmospheric conditions in a laboratory for three weeks after its removal from the reactor, thus allowing the soot to "set up" so as to simulate worst case conditions. The inside wall of the lamp well was thoroughly cleaned with a swab prior to the following test so that only soot on the exterior surface of the well would be observed.

A glass cylinder 5.5 inches (14 cm) in diameter and 30 inches (76.2 cm) high was placed on a large magnetic stirrer. A magnetic stirring bar 4.1 inches (10.4 cm) long and 1.1 inches (2.8 cm) in diameter, and 0.5 oz (15 ml) of cylindrically shaped pieces of PMP about ⅛ inch (0.32 cm) long and ⅛ inch diameter were placed in the glass cylinder. Two gallons (7.6 L) of n-dodecylmercaptan (dodecylthiol) was then added to the glass cylinder.

The quartz lamp well having the soot on its outer surface was then suspended in the cylinder with about 18 inches (45.7 cm) of the lamp well below the surface of the mercaptan. The stirrer was then turned on and the following test results observed.

| Time (Hrs.) | Pellet volume (bulk, cc) | Observation |
| --- | --- | --- |
| 0 | 15 | Began the test |
| 2 | 60 | Beads added, first evidence of soot removal noted. |
| 4 | 240 | Beads added, definite soot removal noted. |
| 6 | 240 | Laminar flow noted, a rod shaped baffle was added. |
| 10.5 | 240 | About 50% soot removal, a channel iron section was installed to replace the rod shape baffle. |
| 16 | 240 | About 70% to 80% soot removal. |
| 32 | 240 | About 95% soot removal at termination of test. |

The area of direct impingement of the pellets on the lamp well was quite small, however, in the area of impingement very little soot remained on the outer surface of the tubular lamp well at the end of the test. The most noticeable soot residue remaining on the lamp well was found in scratches on its surface. The above test results for cleaning a "worst case" lamp well indicate that continuous cleaning in a reactor by impingement of plastic pellets is feasible.

EXAMPLE II

The following example is provided to illustrate the resistance of plastic pellets of PMP/polyethylene/carbon black to chemical attack by the product and the harsh UV reactor environment.

Extruded sample plastic coupons were prepared as follows:

A. 2% carbon black/18% polyethylene/80% PMP (by weight); weight of twelve 2% carbon black coupons—13.492 g/.
B. 1% carbon black/9% polyethylene/90% PMP (by weight); weight of twelve 1% carbon black coupons—15.203 g/.

Sample coupons that could be easily identified according to the carbon black composition were prepared from the above carbon black containing plastic material, put in a metal screen container, and the container holding the coupons was placed inside a commercial size UV reactor for n-dodecyl mercaptan for twenty-three days. On removal of the coupons from the reactor, the following weights were measured:

A. weight of twelve 2% carbon black containing coupons—14.199 g, (change 5.2%).
B. weight of twelve 1% carbon black containing coupons—15.848 g, (change 4.2%).

Four coupons of each type were stored in a bottle for possible future use, and eight of each type of coupon were weighed and returned to the metal screen container. The following weights were measured:

A. weight of eight 2% carbon black containing coupons—10.556 g
B. weight of eight 1% carbon black containing coupons—9.340 g The metal screen container holding eight of each type of coupon was inserted in a UV reactor for n-decyl mercaptan for three days. On removal of the coupons from the reactor the following weights were measured:

A. weight of eight 2% carbon black containing coupons—10.308 g, (change 2.3%).
B. weight of eight 1% carbon black containing coupons—9.105 g, (change 2.5%).

The stability of the plastic pellets in the reaction solution is confirmed by the relatively small weight changes indicated in the above weight test results, and the overall acceptable appearance of the test coupons on completion of the test.

The present invention provides a flexible cleaning system for protective tubular lamp wells used in various sizes of photochemical reactors, wherein the lamp wells are cleaned in place while the UV reactor may be producing a variety of sellable products. In this disclosure there is shown and described only the preferred embodiment of the invention, however, it is to be understood that the invention is suitable for use in various other combinations and environments and changes or modifications within the scope of the inventive concept as expressed herein are possible by those skilled in the art.

That which is claimed is:

1. A photochemical reactor comprising a vessel having an inner wall which defines a chamber for containing a reaction solution, at least one ultraviolet lamp positioned in said chamber for illumination of said chamber, a protective tubular lamp well surrounding said at least one ultraviolet lamp formed of a material transparent to ultraviolet light, and cleaning means for said protective tubular lamp well, said cleaning means comprising:
   (a) a plurality of small solid bodies for suspension in a reaction solution, wherein the size of said small bodies ranges in volume from about 0.003 cc to about 100 cc;
   (b) means for containing said plurality of small bodies within said chamber; and
   (c) means for maintaining said small bodies in continuous turbulent motion in a reaction solution within said chamber so as to cause frequent impacts with the outer surface of said protective tubular lamp well, wherein the impacts of said small bodies with the outer surface of said protective tubular lamp well have sufficient momentum for preventing deposits of material which discolor the surface from adhering to the surface of said protective tubular lamp well so as to maintain transparency of said protective tubular lamp well to ultraviolet light.

2. Apparatus in accordance with claim 1, wherein said material transparent to ultraviolet light comprises quartz.

3. Apparatus in accordance with claim 1, wherein said small bodies are essentially composed of a plastic material selected from the group of plastics consisting of polyethylene and polymethylpentene and combinations thereof.

4. Apparatus in accordance with claim 3 wherein said plastic material includes a minor portion of carbon black.

5. Apparatus in accordance with claim 1, wherein said small bodies have a shape selected from the group of shapes consisting of spherical, cylindrical, conical, elliptical, rectangular and disc.

6. Apparatus in accordance with claim 1, wherein soot is prevented from adhering to the surface of said tubular lamp well.

7. Apparatus in accordance with claim 1, wherein the specific gravity of said small bodies ranges from about 0.6 to about 1.4 and preferably ranges from about 0.7 to 1.3, and most preferably ranges from about 0.80 to about 1.0.

8. Apparatus in accordance with claim 1, wherein the bulk volume of said small bodies for containment in said chamber ranges from about 1/1500 to about 1/4 of the volume of said chamber.

9. Apparatus in accordance with claim 1, wherein said means for maintaining said small bodies is continuous turbulent motion comprises a stirrer operably mounted for rotation in said chamber.

10. Apparatus in accordance with claim 1, wherein illumination from said UV lamp positioned in said chamber catalyzes said reaction solution.

11. Apparatus in accordance with claim 1 wherein said reaction solution produces a mercaptan.

12. A cleaning means in accordance with claim 1, wherein said plurality of small bodies for suspension in said reaction solution each range in volume from about 0.01 cc to about 0.05 cc.

13. A method for preventing deposits of material which would discolor a surface from adhering to the surface of a tubular lamp well mounted in a photochemical reactor, said method comprising the following steps:
   (a) introducing a plurality of small bodies into said reactor, said small bodies ranging in volume from about 0.003 cc to about 100 cc;

(b) containing said plurality of small bodies in said reactor during a reaction; and (c) maintaining said small bodies in continuous turbulent motion in a reaction solution in said reactor so as to cause frequent impacts with the outer surface of said tubular lamp well, wherein the impacts of said small bodies with the surface of said tubular lamp well have sufficient momentum for preventing deposits of material, which would discolor the surface, from adhering to said tubular lamp well, thereby maintaining transparency of said tubular lamp well to ultraviolet light.

14. A method in accordance with claim 13, wherein said reactor includes a stirrer mounted therein, and said step of maintaining said small bodies in continuous turbulent motion comprises stirring said reaction solution containing said plurality of small bodies.

15. A method in accordance with claim 13, wherein said tubular lamp wells comprise quartz glass.

16. A method in accordance with claim 13, wherein said reaction solution produces a mercaptan.

17. A method in accordance with claim 13, wherein said small bodies are formed by combining plastic materials selected from the group of plastics consisting of polyethylene and polymethylpentene and combinations thereof.

18. A method in accordance with claim 17 additionally comprising incorporating a minor portion of carbon black in polymethylpentene for forming said small bodies.

19. A method in accordance with claim 18 wherein the amount of carbon black incorporated in said small bodies ranges from about 1 weight percent to about 2 weight percent.

20. A method in accordance with claim 13, wherein said step of introducing a plurality of small bodies into said reactor comprises introducing small bodies each ranging in volume from about 0.01 cc to about 0.05 cc.

* * * * *